Aug. 2, 1949. E. S. RUSSELL Plant Pat. 859
ANTHEMIS TINCTORIA PLANT
Filed Feb. 18, 1948
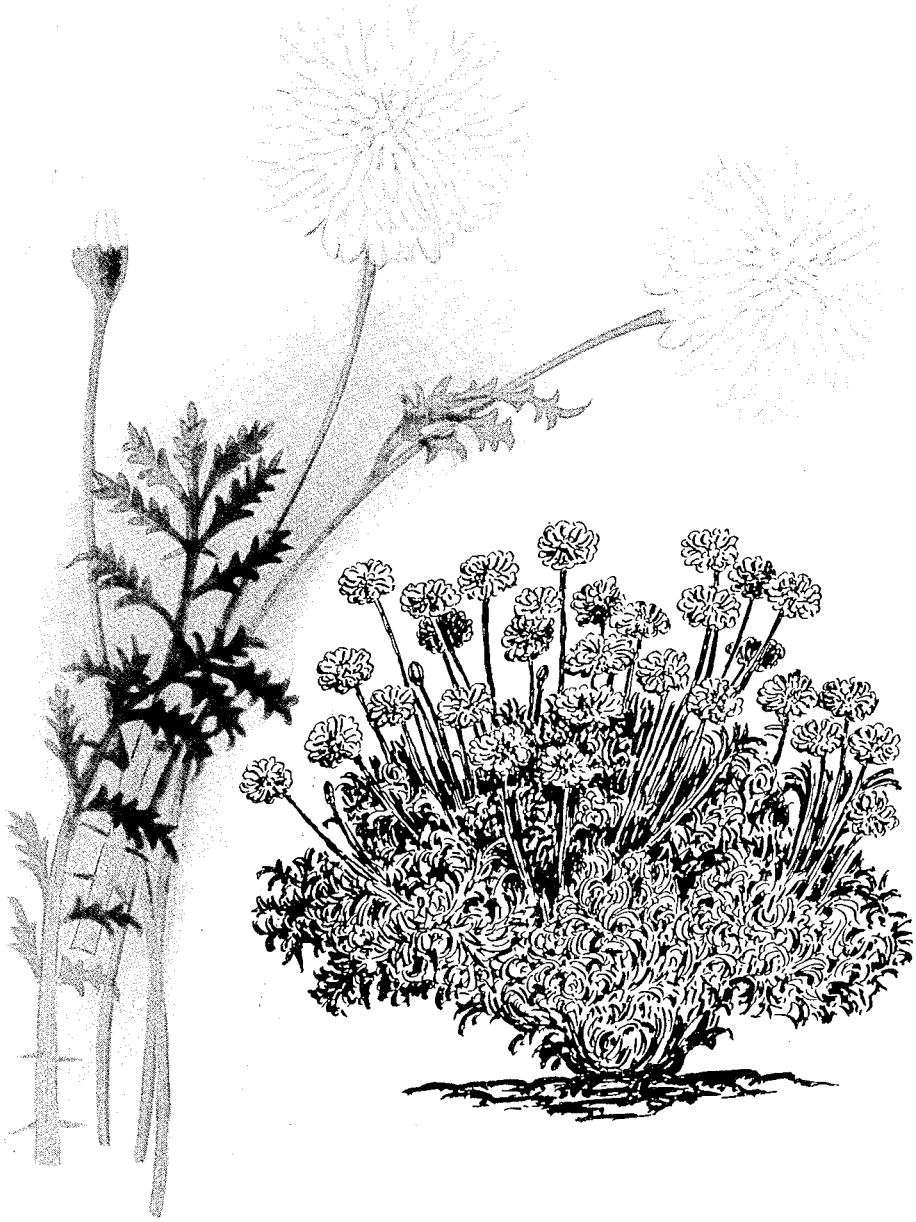
WITNESS
Addison J. Avery
INVENTOR
Ethel Stevenson Russell,
by: John A. Brown,
her ATTY.

Patented Aug. 2, 1949

Plant Pat. 859

UNITED STATES PATENT OFFICE

859

ANTHEMIS TINCTORIA PLANT

Ethel Stevenson Russell, Canton, Pa., assignor, by mesne assignments, to The Wayside Gardens Company, Incorporated, Mentor, Ohio, a corporation of Ohio Application February 18, 1948, Serial No. 9,231

1 Claim. (Cl. 47—60)

This invention relates to a new variety of anthemis tinctoria plant. The variety was produced by a cross between two anthemis tinctoria plants of unknown parentage, the new anthemis tinctoria variety being one of many seedlings resulting.

The new variety was first asexually reproduced at Shelburne, Vermont, by cuttings.

The new variety is illustrated in the drawing wherein a number of stalks with blooms, leaves, and a bud are illustrated by the colored figure and the general appearance of the plant is illustrated by the black and white figure.

The new variety of anthemis tinctoria is shallow rooted and has the usual fibrous mass of roots of the average size. The root resistance to disease and drouth is good, both protected and unprotected, the roots having withstood temperatures as low as ten degrees below zero, Fahrenheit, without ill effects. They thrive best in light warm soils.

The exposed plant structure is generally hardy and herbaceous, slightly recumbent, tough, bushy, compact and clumped in growth. The exposed plant is from four to eight inches in height and about twelve inches in spread, being rather more dwarfed than is usual for anthemis plants. The plant, when not in bloom, is relatively wide and flat but, when in bloom, is globular in form with the blooms carried well above the foliage. It is very vigorous in growth. The resistance of the exposed plant to low temperatures, both protected and unprotected, ranges from good to exceptional. Its resistance to disease and drouth is exceptional and its resistance to wet weather is good. It prefers intense sun with a southern exposure in a well drained or normally drained moderately fertile soil, particularly a sandy loam.

The main stalks of the plant grow singly from the roots and are smooth or slightly hirsute, upright, herbaceous, and slightly branched, being from six to eight inches in length. For an anthemis tinctoria plant they are relatively stiff and tough and adequate to support the foliage and bloom well. The color of the new and old growth is a rather dark grayish green, the color being relatively uniform but slightly lighter in the new growth. The branches are whorled in arrangement and of the usual color and texture. The length of the flower stems is from ten to eighteen inches.

The foliage is dense but lacy. The leaves are whorled in arrangement, of medium quantity, and of the usual shape and color for anthemis tinctoria plants, being slightly lighter in color on the underface than on the upperface. Both the old and the new leaves are a rather dark grayish green. Those on the upper portion of the plant are comparable in color to Maerz and Paul Plate 23–L–5 and those near the base of the plant are comparable to Maerz and Paul Plate 20–K–2. The leaf size is average for the species, ranging from one to three inches in length and from one to two inches in width. They are generally smooth but slightly hirsute on both the upper and lower faces. Their persistency on the plant is excellent.

The plant blooms well in the north temperate zone, preferring the northern section of the United States. It blooms best in a southern or western exposure, in a relatively dry hot season, and in a well drained neutral, relatively poor sandy or rocky soil, or sandy or rocky loam, or relatively light clay loam. Too rich a soil results in a scraggly growth and fewer flowers. An unfavorable growing site reduces the quantity of blooms but does not appreciably affect the color. Excessive shade and moisture greatly reduce the number of blooms but these conditions do not appear to affect the size of the blooms. However, shade and excessive moisture result in blooms of paler color.

The average blooming period is from the first of June to the end of August during which period the plant blooms continuously. Cutting of the blooms increases the blooming period and the number of blooms produced.

The buds are of the usual shape and are borne upright on the stems. The color is golden yellow. The bud has the usual sepals and calyx of anthemis tinctoria plants. The peduncles average from six to eight inches from top leaf to the bloom and are of the usual texture and color. They are relatively strong. The buds are slow to open but open more rapidly in hot weather than in cooler weather.

Each of the blooms averages from one to two inches in diameter and each separate crown of the plant has five to seven blooms. The blooms last for several weeks on the plant and from a week to ten days when cut. They have the normal number of ray petals but are extremely double. Their color is a golden yellow ranging from Maerz and Paul Plate 9′–L′–5 at the base of the petals to Maerz and Paul Plate 9′–L′–6 at the outer extremities of the petals. The general tonality of the blooms from a distance is golden yellow. There is no appreciable change in color of the blooms during the blooming season.

The doubling of the petals produces an unusual arrangement of the center petals resulting in an extremely double bloom which is rounded instead of conical, the latter shape being usual for anthemis tinctoria. So far as is known, no double form of anthemis tinctoria bloom has ever been known. The blooms have from thirty to fifty petaloids in the center and which are very persistent both on the cut and uncut bloom. The boom appears to have no stamen and is sterile. The bloom has a heavy chrysanthemum-like aroma.

The plant is characterized principally by the extreme doubleness of the bloom with its resultant completely different rounded shape compared with the conical shaped blooms of the species generally, the lack of genital organs which eliminates the proliferant seeding, and by the even bright golden yellow color of the blooms as compared to the usual yellow of this species which is several degrees lighter.

Having thus fully shown and described my new variety of anthemis tinctoria plant and method of reproduction, I claim:

The new and distinct variety of anthemis tinctoria plant as described and illustrated, characterized by blooms of an even bright golden yellow throughout, the extreme doubleness of the blooms which results in a completely different and rounded shape instead of the conical shape of the blooms of other anthemis plants, and the absence of genital organs and of the usual proliferant seeding characteristic of anthemis tinctoria plants.

ETHEL STEVENSON RUSSELL.

No references cited.